United States Patent
Holand et al.

(10) Patent No.: US 9,403,721 B2
(45) Date of Patent: Aug. 2, 2016

(54) COMPOSITE CERAMIC MATERIAL COMPRISING ZIRCONIA

(71) Applicant: Ivoclar Vivadent AG, Schaan (LI)

(72) Inventors: Wolfram Holand, Schaan (LI); Elke Signer-Apel, Oberschan (CH); Christian Ritzberger, Grabs (CH); Frank Rothbrust, Frastanz (AT); Heinrich Kappert, Vaduz (LI); Volker Rheinberger, Vaduz (LI); Jerome Chevalier, Rillieu-la Pape (FR); Helen Reveron, Villeurbanne (FR); Nicolas Courtois, Villeurbanne (FR); Ricardo Dellagiacomo, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/515,928

(22) Filed: Oct. 16, 2014

(65) Prior Publication Data
US 2015/0035210 A1 Feb. 5, 2015

Related U.S. Application Data

(62) Division of application No. 13/085,733, filed on Apr. 13, 2011, now Pat. No. 8,889,576.

(30) Foreign Application Priority Data

Apr. 16, 2010 (EP) .................................... 10160162

(51) Int. Cl.
C04B 35/48 (2006.01)
C04B 35/49 (2006.01)
(Continued)

(52) U.S. Cl.
CPC ............... *C04B 35/48* (2013.01); *A61K 6/0008* (2013.01); *A61K 6/0094* (2013.01); *A61K 6/024* (2013.01);
(Continued)

(58) Field of Classification Search
CPC .... C04B 35/48; C04B 35/486; C04B 35/482; C04B 35/488; C04B 35/4885
USPC .................................................. 501/103, 105
See application file for complete search history.

(56) References Cited

U.S. PATENT DOCUMENTS 4,587,225 A * 5/1986 Tsukuma et al. ............. 501/105
4,820,667 A * 4/1989 Tsunekawa et al. .......... 501/104
(Continued)

FOREIGN PATENT DOCUMENTS

| JP | 05301767 | 11/1993 |
| JP | 8-154955 A | 6/1996 |
| WO | 2011000390 A1 | 1/2011 |

OTHER PUBLICATIONS

Morita, K., et al., Synthesis of dense nanocrystalline ZrO2—MgAl2O4 spinel composite, Scripta Materialia, Aug. 2, 2005, vol. 53, pp. 1007-1012.
(Continued)

*Primary Examiner* — Noah Wiese
(74) *Attorney, Agent, or Firm* — Ann M. Knab; Thad McMurray

(57) ABSTRACT

The invention relates to a composite ceramic material which comprises:
(a) a first phase based on zirconia containing $CeO_2$ as stabilizer, and
(b) a second phase based on an aluminate.
The invention also relates to a ceramic powder composition, processes for the preparation of the composite ceramic material and the ceramic powder composition as well as uses thereof.

13 Claims, 1 Drawing Sheet

(51) Int. Cl.

| | | |
|---|---|---|
| *A61K 6/00* | (2006.01) | |
| *A61K 6/02* | (2006.01) | |
| *B82Y 30/00* | (2011.01) | |
| *C01G 9/00* | (2006.01) | |
| *C01G 25/02* | (2006.01) | |
| *C04B 35/488* | (2006.01) | |
| *C04B 35/626* | (2006.01) | |

(52) U.S. Cl.
CPC .............. *A61K 6/0255* (2013.01); *B82Y 30/00* (2013.01); *C01G 9/00* (2013.01); *C01G 25/02* (2013.01); *C04B 35/4885* (2013.01); *C04B 35/6262* (2013.01); *C04B 35/6263* (2013.01); *C04B 35/62685* (2013.01); *C01P 2002/50* (2013.01); *C01P 2002/72* (2013.01); *C01P 2004/62* (2013.01); *C01P 2004/64* (2013.01); *C01P 2006/62* (2013.01); *C01P 2006/63* (2013.01); *C01P 2006/64* (2013.01); *C04B 2235/3206* (2013.01); *C04B 2235/3222* (2013.01); *C04B 2235/3227* (2013.01); *C04B 2235/3229* (2013.01); *C04B 2235/3246* (2013.01); *C04B 2235/3284* (2013.01); *C04B 2235/444* (2013.01); *C04B 2235/5409* (2013.01); *C04B 2235/5445* (2013.01); *C04B 2235/608* (2013.01); *C04B 2235/656* (2013.01); *C04B 2235/6567* (2013.01); *C04B 2235/765* (2013.01); *C04B 2235/77* (2013.01); *C04B 2235/781* (2013.01); *C04B 2235/783* (2013.01); *C04B 2235/785* (2013.01); *C04B 2235/80* (2013.01); *C04B 2235/96* (2013.01); *C04B 2235/9607* (2013.01); *C04B 2235/9661* (2013.01)

(56) References Cited

U.S. PATENT DOCUMENTS

| | | | | |
|---|---|---|---|---|
| 4,880,757 | A | * | 11/1989 | Henslee et al. ............... 501/104 |
| 5,726,110 | A | | 3/1998 | Majumdar et al. |
| 5,728,636 | A | | 3/1998 | Nawa et al. |
| 6,602,813 | B2 | | 8/2003 | Shinji et al. |
| 6,946,417 | B2 | | 9/2005 | Simpson |
| 7,056,851 | B2 | * | 6/2006 | Nawa ........................... 501/105 |
| 7,148,167 | B2 | | 12/2006 | Shikata et al. |
| 7,655,586 | B1 | * | 2/2010 | Brodkin et al. ............... 501/103 |
| 2004/0067839 | A1 | | 4/2004 | Nawa et al. |
| 2005/0272591 | A1 | | 12/2005 | Nawa et al. |
| 2009/0292366 | A1 | | 11/2009 | Burger et al. |
| 2009/0317767 | A1 | * | 12/2009 | Burger et al. .............. 433/201.1 |

OTHER PUBLICATIONS

Miura, M., et al., Formation of plate-like lanthanum-B-aluminate crystal in CE-TZP martix, 6053 Journal of Materials Science, Jan. 1, 1994, vol. 29, No. 1, pp. 262-268.

Tsukuma, K., et al., Mechanical Property & Microstructure of TZP & TZP/Al2O3 Composites, Tokyo Research Center, Material Research Society Symp. Proc., 1987, vol. 78, pp. 123-135.

* cited by examiner

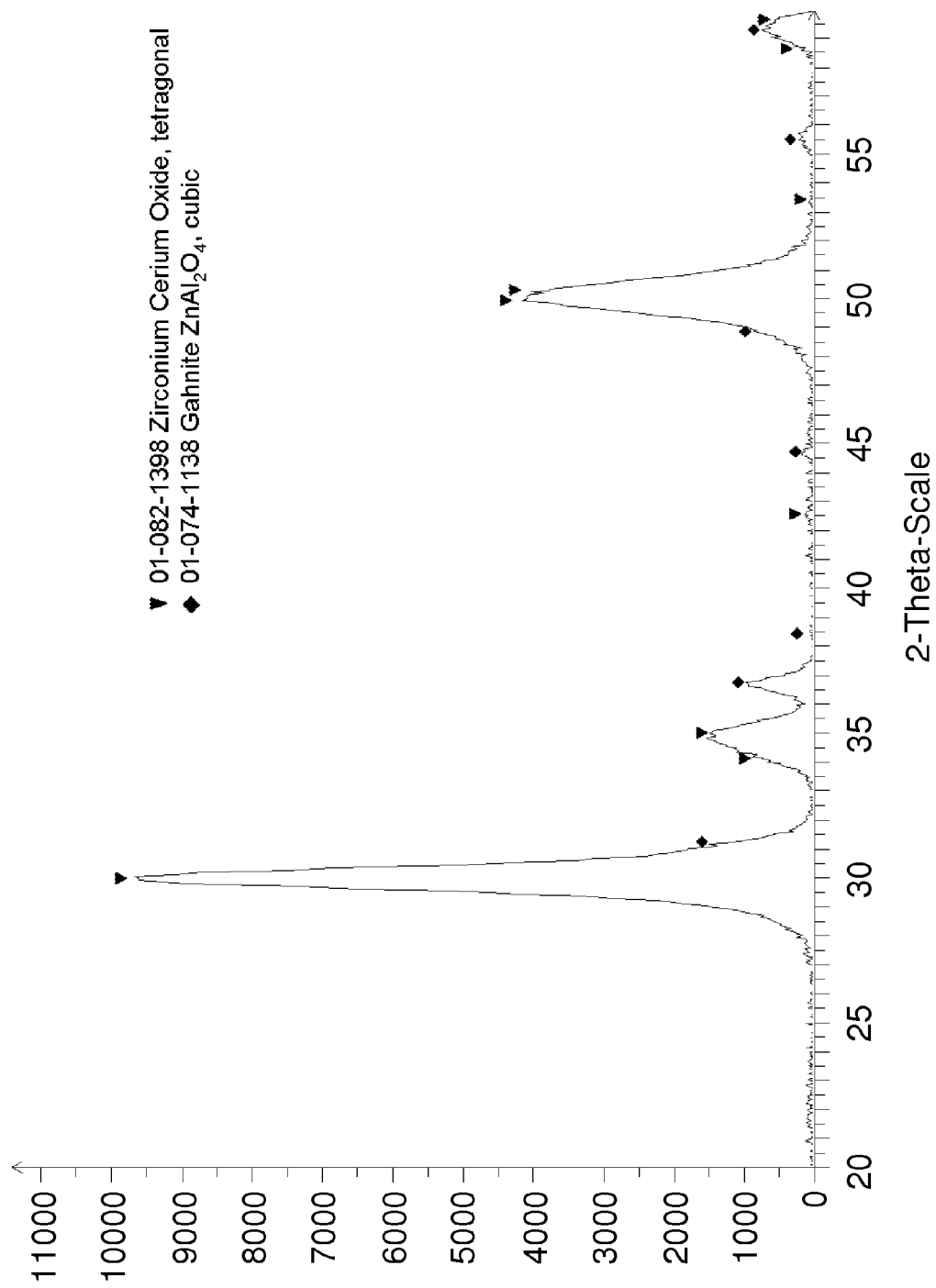

COMPOSITE CERAMIC MATERIAL COMPRISING ZIRCONIA

CROSS-REFERENCE TO RELATED APPLICATIONS

This application is a divisional application of U.S. application Ser. No. 13/085,733, filed Apr. 13, 2011, which claims the benefit of European Patent Application Serial No. 10160162.3, filed Apr. 16, 2010, all of which are hereby incorporated by reference in their entirety.

TECHNICAL FIELD

The invention relates to a composite ceramic material comprising zirconia and to a ceramic powder composition, which are particularly suitable for dental applications, processes for their preparation and uses thereof.

BACKGROUND OF THE INVENTION

Zirconia based ceramics have been used for many years, for instance as structural materials for orthopedic implants and prostheses as well as for dental implants and restorations. Such ceramics typically contain zirconia in its tetragonal form, which is metastable at room temperature and thus requires stabilizers such as $Y_2O_3$.

Ceramic materials based on partially stabilized zirconia, namely yttria stabilized tetragonal zirconia polycrystal (Y-TZP), are widely used and generally have favorable mechanical properties such as very high flexural strength. However, these ceramics exhibit a relatively modest fracture toughness ($K_{IC}$) in the range of 4 to 5 MPa·m$^{0.5}$. Moreover, Y-TZP materials have been found to be subject to the phenomenon of low temperature degradation (LTD), also referred to as aging, especially in the presence of water or a humid environment.

A different type of zirconia ceramics are the ceria stabilized zirconia ceramics (Ce-TZP). While these ceramics can show higher fracture toughness values than Y-TZP materials, they have only a moderate flexural strength, with conventional Ce-TZP ceramics generally exhibiting a flexural strength of not more than 700 MPa. This is insufficient for many medical and dental applications, which typically require a flexural strength of at least 800 MPa.

Yet another type of ceramics are the so-called ceramic matrix composites (CMC), which comprise at least two different crystalline phases. Typical examples are zirconia toughened alumina (ZTA) or alumina toughened zirconia (ATZ), but other matrices, such as SiC or $Si_3N_4$, are also known for this type of material.

U.S. Pat. No. 4,880,757, which is hereby incorporated by reference, discloses composite ceramic materials comprising a zirconia minor phase, which may be stabilized by $Y_2O_3$, and a spinel major phase.

Morita et al. (Scripta Materialia, 2005, 53, 1007-1012) describe a nanocrystalline composite comprising $Y_2O_3$-stabilized tetragonal zirconia and $MgAl_2O_4$ phases. However, the overall mechanical properties of this material are still not fully satisfactory.

U.S. Pat. No. 5,728,636, which is hereby incorporated by reference, describes a ceramic matrix composite consisting of a zirconia matrix stabilized with 8 to 12 mol % $CeO_2$ and 0.05 to 4 mol % $TiO_2$ and having $Al_2O_3$ as second component, which accounts for 0.5 to 50 vol % of the composite. EP 1 382 586 and EP 1 580 178, which are hereby incorporated by reference, describe similar composite materials, which comprise a first phase of zirconia stabilized with 10-12 mol % $CeO_2$ and 20 to 60 or 70 vol % $Al_2O_3$ as a second phase.

One particular disadvantage of $CeO_2$-stabilized zirconia based ceramic matrix composites of the prior art is that their intrinsic colors are unacceptable for dental restorative materials. Furthermore, due to their sensitivity to redox reactions, these materials exhibit pronounced color instability upon heat treatment at low oxygen partial pressure. For instance, when veneering such materials with glass ceramics, the application of vacuum within the firing chamber that is needed to achieve a homogenous densely sintered layering material results in a color change to give a highly unpleasant greenish appearance.

Furthermore, it has been found necessary to fully blast conventional Ce-TZP ceramic frameworks prior to veneering in order to achieve sufficiently high bond strength to the veneering. In comparison to the common instructions for use relating to 3Y-TZP dental materials, this procedure is totally different and might lead to confusion. Another disadvantage is the low wettability of the compositions used in the preparation of the prior art composites, which makes application of a glass-ceramic slurry for instance for veneering much more difficult. Thus, these materials are not suitable for many common dental applications, processes and materials.

SUMMARY OF THE INVENTION

It is therefore an object of the invention to avoid one or more disadvantages of the state of the art described above, and to provide a ceramic material which is particularly suitable for dental applications and products. Such material should exhibit excellent mechanical properties, such as high flexural strength and high fracture toughness, as well as longtime durability, i.e. no or very little low temperature degradation (LTD). Furthermore, it should have intrinsic color matching the shade of natural teeth and should be compatible with common dental applications and materials such as veneering materials of the glass-ceramic type.

BRIEF DESCRIPTION OF THE FIGURES

Further advantages, details and features emerge from the following description of embodiments of the invention on the basis of the drawings, in which:

FIG. 1 shows an x-ray diffraction pattern of a coprecipitated powder composition obtained after calcination.

DETAILED DESCRIPTION

In a first aspect, the invention relates to a composite ceramic material which comprises:
 (a) a first phase based on zirconia containing $CeO_2$ as stabilizer, and
 (b) a second phase based on an aluminate.

The composite ceramic material is generally a sintered ceramic material. Typically, it is a ceramic matrix composite comprising the first phase based on $CeO_2$ stabilized zirconia as matrix phase. It is preferred that the amount of the first phase is more than 50 vol %, preferably 60 to 95 vol %, and more preferably 70 to 84 vol %, particularly more than 50 wt %, preferably 70 to 98 wt %, and more preferably 75 to 84 wt % based on the total ceramic material.

The zirconia is typically mainly in its tetragonal form. It is preferred that the content of tetragonal zirconia is more than 90 vol %, particularly at least 95 vol %, more preferably at least 97 vol %, and most preferably at least 99 vol % based on the total zirconia volume in the ceramic composite.

The zirconia preferably contains 4 to 18 mol %, particularly 6 to 14 mol %, more preferably 8 to 12 mol % $CeO_2$ as stabilizer based on the total amount of stabilized zirconia. According to one embodiment, the zirconia contains 4 to 10 mol %, particularly 5 to 9.9 mol %, more preferably 5 to 9 mol %, most preferably 6 to 8 mol % $CeO_2$ based on the total amount of stabilized zirconia. According to another embodiment, the zirconia contains 6 to 18 mol %, particularly 8 to 16 mol %, and more preferably 10 to 12 mol % $CeO_2$ based on the total amount of stabilized zirconia.

The zirconia may further contain one or more additives, such as one or more additional stabilizers and/or coloring oxides. Suitable further additives include oxides of Y, Ti, Ca, Mg, Pr, Fe, Tb, Mn and Er, particularly $Y_2O_3$ and $TiO_2$. It is preferred that the zirconia contains 0.001 to 1 mol %, particularly 0.005 mol % to 0.5 mol %, and more preferably 0.01 to 0.1 mol % of further additives, particularly coloring oxides, based on the total amount of stabilized zirconia.

The composite ceramic material according to the invention may generally contain phases comprising submicrometric and/or nanometric grains. As used herein, the term "submicrometric" refers to an average grain size of 100 nm to 1 µm and the term "nanometric" refers to an average grain size of less than 100 nm. The term "average grain size" is defined according to ISO standard definition DIN EN 623-3 (2003-01). Determination of the average grain size is carried out on polished and thermally etched samples and involves measurement of the linear intercept sizes of at least 250 grains in a total over at least six fields of view on lines sufficiently long to encompass at least 20 grains, taking random orientations of measurement.

One or more of the phases described herein may be present as two or more separate phases having the same composition but differing in average grain size. For instance, the first phase may be present as two separate phases, one of which is a submicrometric and one of which is a nanometric phase. Likewise, the second phase as well as any further phases may be present as separate submicrometric and nanometric phases. A phase is considered to be present as two or more separate phases having the same composition but differing in average grain size if the particle size distribution of said phase it at least bimodal.

Any phase described herein may be present as an intragranular phase and/or an intergranular phase within another phase comprising bigger particles. As used herein, the term "intergranular phase" refers to a phase having (preferably nanometric) grains which are located between separated grains of another phase. The term "intragranular phase" refers to a phase having (preferably nanometric) grains which are located within bigger grains of another phase.

According to a particular embodiment, the first phase comprises grains having an average grain size of less than 1.5 µm, particularly 100 to 900 nm, and more preferably 150 to 800 nm and/or grains having an average grain size of less than 100 nm, particularly 10 to less than 100 nm, and more preferably 20 to 80 nm.

The composite ceramic material according to the invention further comprises a second phase based on an aluminate. It is preferred that the amount of the second phase is at least 0.1 vol %, preferably at least 1 vol %, more preferably at least 2 vol %, more preferably 5 to 40 vol %, and most preferably 16 to 30 vol %, particularly at least 0.1 wt %, preferably at least 1 wt %, more preferably at least 2 wt %, more preferably 2 to 30 wt %, and most preferably 16 to 25 wt % based on the total ceramic material.

The term "aluminate" as used herein refers to mixed oxides comprising aluminum and at least one further metal. The aluminate is typically a water-free aluminate. Preferred aluminates are of types $M^IAlO_2$, $M^I_5AlO_4$, $M^{II}Al_2O_4$, $M^{II}_3Al_2O_6$, $M^{III}AlO_3$, $M^{II}M^{III}Al_{11}O_{19}$ and mixtures thereof, wherein $M^I$ is a monovalent metal, $M^{II}$ is a divalent metal and $M^{III}$ is a trivalent metal. Suitable examples include $ZnAl_2O_4$, $MgAl_2O_4$, $LaAlO_3$ and $LaMgAl_{11}O_{19}$. Aluminates having a molar ratio of Al to other metal(s) of 5:1 to 1:5, particularly 3:1 to 1:3, and more preferably 2:1 to 1:2, such as 2:1 or 1:1 are preferred.

According to a preferred embodiment, the aluminate is a spinel type aluminate, particularly of type $M^{II}Al_2O_4$. Suitable examples include $ZnAl_2O_4$ and $MgAl_2O_4$.

It is further preferred that the aluminate shows a lower coefficient of thermal expansion (CTE) than the $CeO_2$ stabilized zirconia. Composite ceramic materials comprising such aluminate(s) as second and optionally third phase have been found to exhibit particularly advantageous mechanical properties.

According to a particular embodiment, the second phase comprises grains having an average grain size of less than 1 µm, particularly 100 to 900 nm, more preferably 150 to 800 nm and/or grains having an average grain size of less than 100 nm, particularly 10 to less than 100 nm, more preferably 20 to 80 nm. The second phase, particularly a nanometric second phase, may be present as an intragranular and/or intergranular phase.

The second phase based on an aluminate may optionally comprise further components. It is preferred that the amount of the aluminate is at least 90 wt %, particularly at least 95 wt %, more preferably at least 98 wt %, and most preferably at least 99 wt % based on the total weight of the second phase.

The composite ceramic material may further comprise an optional third phase based on an aluminate which is different from the aluminate of the second phase. Preferably, the amount of the third phase is at least 0.1 vol %, preferably at least 0.5 vol %, more preferably 1 to 15 vol %, most preferably 2 to 10 vol %, particularly at least 0.1 wt %, preferably at least 0.5 wt %, more preferably 1 to 15 wt %, and most preferably 2 to 10 wt % based on the total ceramic material. Preferred aluminates are as defined above for the second phase.

According to a particular embodiment, the third phase comprises grains having an average grain size of less than 1 µm, particularly 100 to 900 nm, more preferably 150 to 800 nm and/or grains having an average grain size of less than 100 nm, particularly 10 to less than 100 nm, and more preferably 20 to 80 nm. The third phase, particularly a nanometric third phase, may be present as an intragranular and/or intergranular phase.

The third phase based on an aluminate may optionally comprise further components. It is preferred that the amount of the aluminate is at least 90 wt %, particularly at least 95 wt %, more preferably at least 98 wt %, and most preferably at least 99 wt % based on the total weight of the third phase.

The composite ceramic material may optionally comprise further aluminate and/or non-aluminate phases.

The composite ceramic material according to the invention has surprisingly been found to provide an advantageous combination of properties and provides both high toughness and strength and has a color that is well suited for dental applications.

In particular, the composite ceramic material typically provides a fracture toughness in the range of 6 to 20 $MPa \cdot m^{0.5}$, preferably 10 to 20 $MPa \cdot m^{0.5}$, and a biaxial flexural strength of more than 600 MPa, preferably more than 900 MPa.

The color displayed by the composite ceramic material is generally close to the color of natural teeth. In particular, the a* value of the material is not lower than −4.0, preferably not lower than −3.0, more preferably not lower than −2.0.

The composite ceramic material has further been found to be essentially unaffected by low temperature degradation (LTD). In particular, the degree of tetragonal to monoclinic transformation measured under the testing conditions defined in standard ISO 13356, i.e. after accelerated aging in steam at 134° C. (±20° C.) under a pressure of 2 bar for a period of 5 hours, is well below the limit of 15 vol %. Preferably, the monoclinic content after exposure to the testing conditions of ISO 13356 is below 5 vol %.

The composite ceramic material according to the first aspect of the invention can be prepared by various methods. A particularly convenient way of preparing the composite ceramic material according to the first aspect of the invention uses a particular ceramic powder composition directly as starting material.

In a second aspect, the invention is therefore directed to a ceramic powder composition comprising:
(c) zirconia containing $CeO_2$ as stabilizer and
(d) an aluminate.

Preferred embodiments of the ceramic powder composition, particularly with regard to composition and the presence and properties of the various phases, are as described for the composite ceramic material according to the first aspect of the invention.

The ceramic powder composition typically contains sub-micrometric and/or nanometric particles. Preferred compositions comprise nanometric zirconia particles containing 4 to 10 mol %, particularly 5 to 9.9 mol %, more preferably 5 to 9 mol %, and most preferably 6 to 8 mol % $CeO_2$ as stabilizer based on the total amount of stabilized zirconia. Compositions comprising nanometric zirconia particles having a specific surface area of 30 to 100 m2/g are particularly preferred. It was surprisingly found that such nanometric zirconia particles can be essentially or entirely of tetragonal form, whereas commercial $CeO_2$-TZP powders like 10Ce-TZP or 12Ce-TZP with specific surfaces from about 5 to below 30 $m^2/g$ always show a certain monoclinic content besides a tetragonal main form.

In a third aspect, the invention is directed to a process for preparing the ceramic powder composition according to the second aspect of the invention, which process comprises:
(i) providing an aqueous solution containing salts of zirconium, cerium, aluminum and at least one further metal;
(ii) adding a base to obtain a precipitate; and
(iii) drying and/or calcining the precipitate.

The at least one further metal represents the second and optionally third metal of the aluminate of the composite ceramic material. Preferably, the at least one further metal is zinc. Suitable counterions include chlorides, oxychlorides, nitrates, oxalates, hydroxides and carbonates, wherein chlorides are preferred. Examples of suitable salts include $ZrCl_4$, $CeCl_3$, $AlCl_3$, $ZnCl_2$, $MgCl_2$, $LaCl_3$ and $ZrOCl_2$. The base is preferably a nitrogen containing base, particularly aqueous ammonia, preferably having a concentration of 20 to 35 wt %, and more preferably 25 to 30 wt %.

Typically, the base is added dropwise to the aqueous salt solution under stirring until a pH of 7.5 to 10, particularly 7.7 to 9, and more preferably 8 to 8.5 has been reached in order to effect precipitation of hydroxides. Optimal pH conditions may vary with the nature of the particular aluminate. The formed precipitate is usually separated from the solution and washed. An optional centrifugation step may be used to concentrate the precipitated hydroxides and facilitate their drying. The precipitated hydroxides are then dried, particularly at a temperature of 100 to 120° C. for 12 to 48 h, optionally milled and finally calcined, particularly at a temperature of 500 to 900° C. for 1 to 3 hours.

The above process provides a multi-coprecipitation technology allowing for parallel coprecipitation of at least two distinct crystal phases, namely at least a $CeO_2$-stabilized zirconia phase and an aluminate phase, such as a $ZnAl_2O_4$ phase, in a single processing step. It has surprisingly been found that in the above process, the cerium ions are coprecipitated with the zirconium ions to form the first phase, whereas the ions of the at least one further metal are coprecipitated with the aluminum ions to form a distinct second phase. In particular, the finding that the at least one further metal, such as zinc, is incorporated into the aluminate phase rather than the zirconia phase, was entirely unexpected in view of the generally high tendency of $ZrO_2$ to incorporate any available ions into its crystal lattice. The multi-coprecipitation technology according to this aspect of the invention thus allows for the preparation of a ceramic powder composition directly suitable for the preparation of the composite ceramic material according to the first aspect of the invention in a single coprecipitation step starting from a single solution of metal salts.

In a fourth aspect, the invention relates to a process for the preparation of the composite ceramic material according to the first aspect of the invention, which process comprises:
(i) providing a ceramic powder composition according to the second aspect of the invention;
(ii) optionally forming a ceramic body; and
(iii) sintering the ceramic powder composition or the ceramic body.

According to one embodiment, the ceramic powder composition can be directly used to form the ceramic body, for instance by dry pressing and/or cold isostatic pressing. According to a preferred embodiment, the ceramic powder composition is used in the form of granules, particularly spray-dried granules. Alternatively, the ceramic powder composition can be used in the form of an aqueous slurry as described in more detail below.

In a fifth aspect, the invention relates to an alternative process for the preparation of the composite ceramic material according to the first aspect of the invention, which process comprises:
(i) providing a first slurry comprising zirconia containing $CeO_2$ as stabilizer, a second slurry comprising an aluminate and optionally a third slurry comprising an aluminate which is different from the aluminate of the second slurry;
(ii) mixing the first slurry with the second and optionally third slurry to obtain a mixed slurry;
(iii) forming a ceramic body; and
(iv) sintering the ceramic body.

It is preferred that each slurry has a solid content of 20 to 80 wt %, particularly 30 to 70 wt %, and more preferably 35 to 65 wt %. It is also preferred that each slurry has a solid content of 5 to 60 vol %, particularly 10 to 50 vol %, and more preferably 15 to 55 vol %. Slurries may further comprise a dispersing agent. Suitable dispersing agents include ammonium polyacrylates, such as Darvan 821A (R.T. Vanderbilt Company Inc., USA), sodium polyacrylates, sodium polymethacrylates, ammonium polymethacrylates, tetramethylammonium hydroxide, triammonium citrate and polycarboxylic acids. The dispersing agent is typically used in an amount of 0.1 to 10 wt %, particularly 0.3 to 9 wt. %, and more preferably 0.5 to 7 wt % based on the weight of the slurry. The pH of each slurry is independently adjusted to 8 to 13, particularly 9 to 12, and more preferably 10 to 11. Preferably, the difference in the pH values of the respective slurries is between 0 and 3, particularly between 0.5 and 2.5, and more preferably between 1 and 2. Quaternary organic ammonium hydroxides, such as tetramethylammonium hydroxide (TMAH), are particularly useful for pH adjustment.

Each slurry is preferably milled before mixing to reduce the particle size. The slurries are mixed in appropriate amounts to give a mixed slurry having the intended ratio of $CeO_2$-stabilized zirconia to aluminate(s). The mixed slurry can be further milled to reduce the particle size.

An amount of an anti-foaming agent may be added to the mixed slurry. Suitable anti-foaming agents include alkyl polyalkylene glycolethers, such as Contraspum K 1012 (Zschimmer & Schwarz, Germany). Finally, the mixed slurry can be degassed under vacuum.

It has surprisingly been found that in spite of their significantly different chemical nature, the separate slurries used in the above process can be stabilized and adjusted to be compatible with one another and can be directly mixed to obtain a mixed slurry which is ready for use in the preparation of the composite ceramic material according to the first aspect of the invention.

$CeO_2$-stabilized zirconia and aluminates for use in the process according to the fifth aspect of the invention may be commercially available or may be prepared according to various methods.

According to one embodiment, an aluminate may be prepared from an aqueous solution containing salts of aluminum and at least one further metal representing the second and optionally third metal of the aluminate, and adding a base to obtain a precipitate. Suitable counter-ions include chlorides and nitrates, wherein chlorides are preferred. Examples of suitable salts include $AlCl_3$, $ZnCl_2$, $MgCl_2$ and $LaCl_3$. The base is preferably aqueous ammonia, preferably having a concentration of 20 to 35 wt %, and more preferably 25 to 30 wt %. Typically, the base is added dropwise to the aqueous salt solution under stirring up to a pH of 8 to 12, particularly 9 to 11, to effect precipitation of hydroxides. Optimal pH conditions may vary with the nature of the particular aluminate. The formed aqueous gel precipitate is separated from the solution and washed. The hydroxides are then dried, milled and finally calcined.

According to another embodiment, an aluminate may be prepared by heat treatment of a mixture of precursor compounds of aluminum and the metal(s) representing the second and/or optionally third metal of the aluminate. Suitable precursor compounds include carbonates, oxides, hydroxides, mixed oxide/hydroxides and hydrates thereof. Examples of precursor compounds are $AlOOH.H_2O$, $MgCO_3$, $ZnO$ and $La_2O_3$. Precursors may be mixed in a rotator mill and subsequently dry milled in a centrifugation mill. The obtained activated powder can be heat treated, preferably at a temperature of 1200 to 2000° C. and more preferably 1500 to 1700° C., and finally crushed, deagglomerated and sieved (preferably <90 µm). Preferably, the obtained aluminate powder is further milled to a $d_{50}$ value of less than 1 µm.

In the processes according to the fourth and fifth aspects of the invention, formation of a ceramic body may be effected using various methods. Preferably, an aqueous slurry is used to obtain spray-dried granules, which granules are subsequently used to form a ceramic body, for instance by dry pressing and/or cold isostatic pressing. Alternatively, an aqueous slurry can be used to form a ceramic body using for instance a slip casting technique, filter pressing or a rapid prototyping technique, such as inkjet printing or stereo lithography.

After its formation the ceramic body is typically debindered and pre-sintered. Debindering is typically performed at a temperature in the range of from 450 to 700° C. It is preferred that the debindered ceramic body has a density in the range of about 45 to about 60% of the theoretical density (TD).

Pre-sintering conditions should usually be adapted to obtain a hardness allowing for further machining into a desired shape in an easy manner without undue wear of the tools and within short times. Typically, the hardness after pre-sintering should be in the range of 300 to 1000 MPa, preferably 500 to 700 MPa, measured as HV2.5 (Vickers hardness using a load of 2.5 kg). Pre-sintering is generally performed at a temperature in the range of from 700 to 1200° C. The exact temperature and hold time should be adapted to the composition and grain size in order to provide the desired hardness.

Prior to final sintering, the pre-sintered ceramic body, particularly a ceramic blank, can be shaped to a desired geometry e.g. by milling or grinding, particularly by machining using CAD/CAM technology, or by hot pressing.

Sintering may be carried out in a conventional sintering furnace. Suitable sintering conditions include sintering at a temperature of 1000 to 1600° C., preferably 1100 to 1550° C. for a time of 15 min to 72 hours, particularly 30 minutes to 24 hours, more preferably 2 to 10 hours. A sintering temperature of 1200 to 1300° C. is particularly preferred for composites having phases comprising nanometric particles. A sintering temperature of 1400 to 1500° C. is particularly preferred for composites having phases comprising submicrometric particles.

Preferred methods use a heating rate of about 1 to 40 K/min up to 1100 to 1500° C., a dwell time of about 2 to 10 hours and a cooling rate of approximately 2 to 10 K/min. It is preferred that the final composite ceramic material has a density of more than 95%, particularly more than 97%, and more preferably more than 98% of the theoretical density. Surprisingly, sintering of the composite ceramic material of the invention can be achieved at significantly lower temperatures as compared to conventional zirconia ceramics such as 3Y-TZP.

The composite ceramic material according to the first aspect of the invention is preferably in the form of a ceramic blank or body which can be shaped in a presintered state to a dental restoration by e.g. milling or grinding, preferably by machining using CAD/CAM technology.

The invention also relates to a use of the composite ceramic material according to the first aspect of the invention or of the ceramic powder composition according to the second aspect of the invention as dental material, and in particular for the preparation of dental restorations, preferably dental frameworks, dental abutments and dental implants, particularly high toughness frameworks and abutments. Such dental restorations are characterized inter alia in maintaining color stability throughout multiple firings and providing good wettability e.g. for veneering materials like glass-ceramics.

In another aspect, the invention relates to a use of the composite ceramic material according to the first aspect of the invention or of the ceramic powder composition according to the second aspect of the invention for rapid prototyping, stereo lithography or inkjet printing.

The invention is further illustrated by the following examples.

EXAMPLES

Unless indicated otherwise, the following methods of measurement were used throughout the examples.

Color Measurements

Color measurements were carried out using a Konica-Minolta CM3700d spectrometer. Optical values L, a and b were determined in accordance with standards DIN 5033 or DIN6174. The CR value, which is a measure of opacity, was determined in accordance with standard BS 5612. Samples having a diameter of 20 mm and a height of 2 mm with polished surface (SiC paper of 1000 grid) were used for measurements.

Fracture Toughness

Fracture toughness was determined as $K_{IC}$ (critical stress intensity factor) using a Zwick Universal Testing Machine ZHUO.2 with a Vickers indenter applying a load of 196 N. The crack length was measured by light microscopy. Fracture toughness was calculated according to the Niihara equation. Vickers hardness was estimated as HV20 (Vickers hardness using a load of 20 kg). Discs having a diameter of 13 mm, a height of about 5 mm were ground and polished with different diamond slurries down to 0.5 μm to obtain parallel surfaces.

Flexural Strength

Flexural strength was measured according to ISO6872 using biaxial samples (13 mm in diameter, height of 1.2 mm). Samples were pre-sintered at 900° C./2 h, pre-grinded using SiC paper (1000 grid). After the final sintering step the samples were measured as fired.

Coefficient of Thermal Expansion (CTE)

CTE was measured according to standard ISO6872:2008 using sintered samples and employing a Netzsch DIL 402C dilatometer in the range of 20 to 700° C. with a heating rate of 5 K/min. The geometry of the sample was according to the standard.

Low Temperature Degradation (LTD)

LTD was measured according to standard ISO13356 on samples which were prepared as described for biaxial strength determination. Specimens were tested in an autoclave (pressure of 2 bar, steam 134±2° C.) for a period of 5 h. The change of the volume fraction of monoclinic modification was determined by X-ray diffraction.

Example 1

CMC Consisting of Two Crystalline Phases (8Ce-TZP/ZnAl$_2$O$_4$) Using One-Step Process to Prepare Ceramic Powder Composition Ceramic Powder Composition A ceramic powder composition comprising 8Ce-TZP and ZnAl$_2$O$_4$ was prepared by coprecipitation from a solution of precursors. ZrCl$_4$ (254.16 g), CeCl$_3$.7H$_2$O (35.34 g), AlCl$_3$.6H$_2$O (129.83 g) and ZnCl$_2$ (36.64 g) were dissolved in de-ionized water. Ammonia (28 vol % aqueous solution) was added gently under vigorous stirring with an overhead stirrer until a pH of 8 was reached.

Precipitated hydroxides were separated and repeatedly rinsed with de-ionized water and subsequently with ethanol. A centrifugation step was provided to concentrate the hydroxides and facilitate their drying. Centrifugation was performed in Allegra 25R equipment from Beckman-Coulter at 4000 rpm for 10 minutes. The concentrate obtained after centrifugation was dried in a furnace at 110° C. for 24 h, then milled for 0.5 h in a Retsch KM100 apparatus using a zirconia mill to prevent contamination, and finally calcined at 700° C. for 2 h. Finally, the calcined powder composition was subjected to a second milling for 0.5 h in the zirconia mill.

The chemical composition of the obtained ceramic powder composition corresponded to 67.2 wt % ZrO$_2$ (including HfO$_2$, which may be present together with the ZrO$_2$ in an amount of up to 5 wt % based on the total weight of ZrO$_2$ and HfO$_2$), 8.15 wt % CeO$_2$ and 24.65 wt % ZnAl$_2$O$_4$.

The coprecipitated powder composition obtained after calcination was also analyzed by X-ray diffraction using a Bruker D8 apparatus. FIG. 1 shows the corresponding XRD pattern.

As can be seen from FIG. 1, the powder composition essentially contained two distinct crystal phases, namely tetragonal Ce-TZP and ZnAl$_2$O$_4$. Only cerium, but substantially no zinc was found to be incorporated into the lattice of the zirconia crystals. Thus, the coprecipitation surprisingly resulted directly in the formation of two separate crystalline phases.

Ceramic Preparation

The ceramic powder composition prepared above (100 g) was dispersed in water (0.096 l) at pH 9 together with (4 g) of a commercial ammonium polyacrylate salt (Darvan 821A) and milled by attrition for 6 hours.

The obtained slurry was dried at 50° C. for 24 hours. A weakly agglomerated powder was obtained, which was crushed manually. Using a die press apparatus and a mold, a pressure of 50 MPa was applied to prepare a disk having a diameter of 16 mm and a thickness of 5.5 mm. The disk was placed into a sealed vacuum package and treated with a cold isostatic press apparatus under a pressure of 350 MPa. The resulting pellet was sintered at 1250° C. for 10 hours in air.

To determine the geometric density of the intermediate and final ceramic, the prepared disks were measured after die pressing and cold isostatic pressing. An Archimedes method described in ASTM C373-88 (2006) was used to measure the density of the sintered body. The results are shown below, wherein the term "geometric" refers to a measurement of disk dimension to estimate the density, and the term "ASTMC373" refers to an Archimedes method as described in ASTM C373-88 (2006):

| Processing step | Density (% TD) |
| --- | --- |
| Die pressing | 32.5 (geometric) |
| Cold isostatic pressing (CIP) | 45 (geometric) |
| Final sintering | 95 (ASTMC373) |

The results of the density measurements reflect the increase of density during the different preparation steps from uniaxial die pressing to cold isostatic pressing. The increase of density of up to 45% of the theoretical density allowed to obtain a density of up to 95% of the theoretical density in the final sintering step.

The morphology of the composite ceramic material was determined by XRD. The obtained XRD spectrum demonstrates that the material comprises tetragonal crystals as main crystal phase. On the basis of this XRD data the monoclinic content was estimated to be below 2 vol %. Thus, the crystalline phases found in the composite ceramic material are essentially only tetragonal CeO$_2$-stabilized zirconia and ZnAl$_2$O$_4$.

Both phases were found to have grain sizes between 50 and 500 nm with an average grain size of 155±35 nm. The phases were homogenously distributed within one another.

The composite ceramic material had a Vickers hardness of 10.8±0.4 GPa. Based on this value, the fracture toughness was determined to be 14.1±0.8 MPa·m$^{0.5}$. The measurement was repeated on a sample with 10 indentations to find a hardness of 10.5±0.1 GPa corresponding to a fracture toughness of 13.8±1.4 MPa·m$^{0.5}$. Finding such high fracture toughness in a ceramic material having an average grain size of less than 200 nm was surprising for this type of composite material.

The coefficient of thermal expansion (CTE) was determined in the range of 100 and 600° C. using a NETZSCH DIL 402C dilatometer to find a CTE of $11.5 \cdot 10^{-6}$ $K^{-1}$. The sample geometry was in accordance with dental standard ISO 6872: 2008.

Upon visual inspection, the composite ceramic material was found to have a color closely matching the color of natural teeth. In contrast to this, a conventional 12Ce-TZP ceramic prepared from commercial raw material from Daiichi was found to show a dark yellow color.

Table 1 shows color properties of the composite ceramic material obtained in Example 1 as compared with the conventional 12Ce-TZP ceramic.

TABLE 1

| Optical parameter | L* | a* | b* |
|---|---|---|---|
| Example 1 | 97.09 | −2.41 | 12.97 |
| 12Ce-TZP | 87.10 | −2.12 | 21.17 |

Example 2

Preparation of Aluminate Starting Powders by Precipitation from Precursor Solution Example 2A $MgAl_2O_4$ $MgCl_2 \cdot 6H_2O$ (29.47 g) and $AlCl_3 \cdot 6H_2O$ (70 g) were dissolved in 3 l of de-ionized water under magnetic stirring to obtain aqueous solution having a pH of about 3.5. Ammonia (28 vol % aqueous solution) was added dropwise under continued stirring until a pH of 11 was reached to precipitate an aqueous gel. The gel precipitate was isolated and washed with de-ionized water until the wash filtrate no longer caused precipitation when contacted with silver nitrate solution in order to effect complete removal of chloride ions. The gel precipitate was dried at 80° C. for 24 h, milled for 1 min and sieved (<90 μm). Finally, the obtained powder was calcined at 800° C. for 1 h to give a starting powder of $MgAl_2O_4$.

Example 2B $ZnAl_2O_4$

Generally following the procedure described for Example 2A but using $ZnCl_2$ (18.59 g) and $AlCl_3 \cdot 6H_2O$ (65.85 g) as starting materials, adjusting the amount of ammonia to give a pH of 9 and performing the final calcination at 700° C. for 2 h, a starting powder of $ZnAl_2O_4$ was obtained.

Example 2C $LaMgAl_{11}O_{19}$

Generally following the procedure described for Example 2A but using $LaCl_3 \cdot 6H_2O$ (21.31 g), $MgCl_2 \cdot 6H_2O$ (12.23 g) and $AlCl_3 \cdot 6H_2O$ (110.12 g) as starting materials and adjusting the amount of ammonia to give a pH of 9.5, a starting powder of $LaMgAl_{11}O_{29}$ was obtained.

Example 2D $LaAlO_3$

Generally following the procedure described for Example 2A but using $LaCl_3 \cdot 6H_2O$ (50 g) and $AlCl_3 \cdot 6H_2O$ (49.22 g) as starting materials and adjusting the amount of ammonia to give a pH of 10, a starting powder of $LaAlO_3$ was obtained.

Example 3

Preparation of Aluminate Starting Powders by Heat Treatment of Precursors

Example 3A $MgAl_2O_4$

MgCO3 (65.73 g) and $AlOOH \cdot H_2O$ (107.5 g) were mixed in a rotator mill for 20 min and subsequently dry milled for 10 min in a centrifugation mill at 150 rpm. The obtained activated powder was heat treated at 1600° C. for 6 h and finally crushed, deagglomerated and sieved (<90 μm). The resulting powder had a d50 value of about 5 μm (meaning that 50% by volume of the particles has a particle size of below 5 μm). The powder was further milled to obtain a starting powder of $MgAl_2O_4$ having a $d_{50}$ value of less than 1 μm.

Example 3B $ZnAl_2O_4$

Generally following the procedure described for Example 3A but using ZnO (44.39 g) and $AlOOH \cdot H_2O$ (83.42 g) as starting materials, a starting powder of $ZnAl_2O_4$ was obtained.

Example 3C $LaMgAl_{11}O_{19}$

Generally following the procedure described for Example 3A but using $La_2O_3$ (21.31 g), $MgCO_3$ (12.23 g) and $AlOOH \cdot H_2O$ (110.12 g) as starting materials, a starting powder of $LaMgAl_{11}O_{19}$ was obtained.

Example 4

Slurry Preparation of Composite Ceramic Materials

Example 4A

Ceramic Matrix Composite of 8Ce-TZP (Zirconia Stabilized with 8 Mol % $CeO_2$) with 15 wt % $MgAl_2O_4$ Matrix Slurry:

72 g of a nanometric 8Ce-TZP powder having a specific surface area of about 55 $m^2$/g were milled in 113.5 ml de-ionized water for 4 h (750 rpm, 500 g zirconia beads) to obtain an average grain size of 15 to 20 nm. 4.5 g of Darvan 821A (R.T. Vanderbilt Company Inc., USA) were added as dispersing agent. The pH was adjusted to about 9 using 2 g of a 1.0 M aqueous tetramethylammonium hydroxide (TMAH) solution.

Second Component Slurry:

33.3 g of a commercial $MgAl_2O_4$ powder (Nanostructured & Amorphous Materials Inc., USA) were milled in 162 ml of de-ionized water for 1 h (750 rpm, 500 g zirconia beads). 1.8 g of Darvan 821A were added as dispersing agent. The pH was adjusted to about 10 using a few droplets of a 1.0 M aqueous tetramethylammonium hydroxide (TMAH) solution.

75.2 g of the second component slurry were mixed with the matrix slurry. A few droplets of Contraspum K1012 (Zschimmer & Schwarz, Germany) were added, and the slurries were mixed for a further 30 min and then degassed under vacuum.

5 ml of the obtained mixed slurry were filled into a metal form having a diameter of 16 mm and pressed uniaxially using a hydraulic filter pressing unit with a load of 60 MPa. The samples were then carefully dried for 12 hours and further densified by a cold isostatic pressing (CIP) process using a load of 200 MPa.

After densification the samples were debindered at 500° C. for 30 min (heating rate 1 K/min) and finally sintered at 1200° C. for 2 h.

XRD analysis of the obtained ceramic matrix composite showed a tetragonal zirconia phase and a $MgAl_2O_4$ phase. The zirconia was surprisingly found to consist entirely of tetragonal zirconia. The composite had a density of 96% of the theoretical density and was of ivory color.

Example 4B

Ceramic Matrix Composite of 10Ce-TZP (Zirconia Stabilized with 10 Mol % $CeO_2$) with 12 wt % $MgAl_2O_4$ Matrix Slurry:
100 g of a commercial nanometric 10 Ce-TZP powder (Daiichi, Japan) were milled in 90 ml of de-ionized water for 4 h (750 rpm, 700 g zirconia beads). 6.25 g of Darvan 821A were added as dispersing agent. The pH was adjusted to about 10 using 3.75 g of a 1.0 M aqueous tetramethylammonium hydroxide (TMAH) solution.

Second Component Slurry:
A second component slurry of $MgAl_2O_4$ was prepared as described in Example 4A.

80.8 g of the second component slurry were mixed with the matrix slurry. A few droplets of Contraspum K1012 were added, and the slurries were mixed for a further 30 min and then degassed. The obtained mixed slurry had a solid content of about 40 wt %. The mixed slurry was densified by filter pressing and cold isostatic pressing as described in Example 4A.

After densification the samples were debindered at 500° C. for 30 min (heating rate 1 K/min) and finally sintered at 1400° C. for 2 h.

XRD analysis of the obtained ceramic matrix composite showed a tetragonal zirconia phase and a $MgAl_2O_4$ phase. The composite had a density of 97% of the theoretical density and was of ivory color.

Example 4C

Ceramic Matrix Composite of 10Ce-TZP (Zirconia Stabilized with 10 Mol % $CeO_2$) with 20 wt % $LaMgAl_{11}O_{19}$ Matrix Slurry:
A matrix slurry of 10Ce-TZP was prepared as described in Example 4B.

Second Component Slurry:
65 g of a calcinated $LaMgAl_{11}O_{19}$ powder were milled in 35 ml of de-ionized water for 4 h (750 rpm, 460 g zirconia beads). 0.23 g of Darvan 821A were added as dispersing agent. The pH was adjusted to about 12 with 3.2 g of a 1.0 M aqueous tetramethylammonium hydroxide (TMAH) solution.

40 g of the second component slurry were mixed with the matrix slurry. A few droplets of Contraspum K1012 were added, and the slurries were mixed for a further 30 min and then degassed. The obtained mixed slurry had a solid content of about 52 wt %. The mixed slurry was densified by filter pressing and cold isostatic pressing as described in Example 4A.

After densification the samples were debindered at 500° C. for 30 min (heating rate 1 K/min) and finally sintered at 1400° C. for 2 h.

XRD analysis of the obtained ceramic matrix composite showed a tetragonal zirconia phase and a $LaMgAl_{11}O_{19}$ phase. The composite had a density of 97% of the theoretical density and was of ivory color.

Example 4D

Ceramic Matrix Composite of 12Ce-TZP (Zirconia Stabilized with 12 Mol % $CeO_2$) with 20 wt % $LaMgAl_{11}O_{19}$ Matrix Slurry:
100 g of a commercial 12 Ce-TZP powder (Daiichi, Japan) were milled in 42.5 ml of de-ionized water for 4 h (750 rpm, 500 g zirconia beads). 3.75 g of Darvan 821A were added as dispersing agent. The pH was adjusted to about 10 using 3.75 g of a 1.0 M aqueous tetramethylammonium hydroxide (TMAH) solution.

Second Component Slurry:
A second component slurry of $LaMgAl_{11}O_{19}$ was prepared as described in Example 4C.

40 g of the second component slurry were mixed with the matrix slurry. A few droplets of Contraspum K1012 were added, and the slurries were mixed for a further 30 min and then degassed. The obtained mixed slurry had a solid content of about 52 wt %. The mixed slurry was densified by filter pressing and cold isostatic pressing as described in Example 4A.

After densification the samples were debindered at 500° C. for 30 min (heating rate 1 K/min) and finally sintered at 1500° C. for 30 min.

XRD analysis of the obtained ceramic matrix composite showed a tetragonal zirconia phase and a $LaMgAl_{11}O_{19}$ phase. The composite had a density of 97.8% of the theoretical density and was of ivory color.

Vickers hardness was measured to be 11700 MPa. Fracture toughness was 6.4 MPa·m$^{0.5}$. Flexural strength was measured to be 640±90 MPa.

Optical values were L*=94.81, a*=−1.36, b*=9.23 and CR=99.93%. The CTE measured in the range of 100 to 600° C. was 12.5 10$^{-6}$/K.

Example 4E

Ceramic Matrix Composite of 12Ce-TZP (Zirconia Stabilized with 12 Mol % $CeO_2$) with 2.5 wt % $MgAl_2O_4$ Matrix Slurry:
A matrix slurry of 12Ce-TZP was prepared as described in Example 4D.

Second Component Slurry:
A second component slurry of $MgAl_2O_4$ was prepared as described in Example 4A.

16 g of the second component slurry were mixed with the matrix slurry. A few droplets of Contraspum K1012 were added, and the slurries were mixed for a further 30 min and then degassed. The obtained mixed slurry had a solid content of about 54 wt %. The mixed slurry was densified by filter pressing and cold isostatic pressing as described in Example 4A.

After densification the samples were debindered at 500° C. for 30 min (heating rate 1 K/min) and finally sintered at 1500° C. for 30 min.

XRD analysis of the obtained ceramic matrix composite showed a tetragonal zirconia phase and a $MgAl_2O_4$ phase. The composite had a density of 98.5% of the theoretical density and was of yellowish color.

Vickers hardness was measured to be 10300 MPa. Fracture toughness was 9.0 MPa·m$^{0.5}$. Flexural strength was measured to be 950±35 MPa. Optical values were L*=93.22, a*=−3.01, b*=13.91 and CR=99.70%. The CTE measured in the range 100 to 600° C. was 12.96 10$^{-6}$/K.

Example 4F

Ceramic Matrix Composite of 12Ce-TZP (Zirconia Stabilized with 12 Mol % $CeO_2$) with 6 wt % $MgAl_2O_4$ and 2 wt % $LaAlO_3$ Matrix Slurry:
A matrix slurry of 12Ce-TZP was prepared as described in Example 4D.

Second Component Slurry:
A second component slurry of $MgAl_2O_4$ was prepared as described in Example 4A.

Third Component Slurry:
72 g of a commercial $LaAlO_3$ powder (Treibacher Industrie AG, Austria) were milled in 114.2 ml of de-ionized water for 4 h (750 rpm, 500 g zirconia beads). 1.8 g of Darvan 821A were added as dispersing agent. The pH was adjusted to 10 using 4.0 g of a 1.0 M aqueous tetramethylammonium hydroxide (TMAH) solution.

40 g of the second component slurry and 6.0 g of the third component slurry were mixed with the matrix slurry. A few droplets of Contraspum K1012 were added, and the slurries were mixed for a further 30 min and then degassed. The obtained mixed slurry had a solid content of about 54 wt %. The mixed slurry was densified by filter pressing and cold isostatic pressing as described in Example 4A.

After densification the samples were debindered at 500° C. for 30 min (heating rate 1 K/min) and finally sintered at 1500° C. for 30 min.

XRD analysis of the obtained ceramic matrix composite showed a tetragonal zirconia phase, a $MgAl_2O_4$ phase and a $LaAlO_3$ phase. The composite had a density of 98% of the theoretical density and was of yellow color.

The properties of the ceramic matrix composites obtained according to examples 1 and 4A to 4F are summarized in Table 2.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

TABLE 2

| Example | 1 | 4A | 4B | 4C | 4D | 4E | 4F |
|---|---|---|---|---|---|---|---|
| Matrix phase | 8Ce-TZP | 8Ce-TZP | 10Ce-TZP | 10Ce-TZP | 12Ce-TZP | 12Ce-TZP | 12Ce-TZP |
| Second phase | $ZnAl_2O_4$ | $MgAl_2O_4$ | $MgAl_2O_4$ | $LaMgAl_{11}O_{19}$ | $LaMgAl_{11}O_{19}$ | $MgAl_2O_4$ | $MgAl_2O_4$ |
| Third phase | — | — | — | — | — | — | $LaAlO_3$ |
| Second phase content (wt %) | 24 wt % | 15 wt % | 12 wt % | 20 wt % | 20 wt % | 2.5 wt % | 6 wt % |
| Third phase content (wt %) | — | — | — | — | — | — | 2 wt % |
| Second and third phase content (vol %) | 30 vol % | 26 vol % | 20 vol % | 29 vol % | 29 vol % | <5 vol % | 12 vol % |
| Sintering conditions | 1250° C./ 10 h | 1250° C./ 10 h | 1400° C./ 2 h | 1400° C./ 2 h | 1500° C./ 30 min | 1500° C./ 30 min | 1500° C./ 30 min |
| Density | 95.4% TD | 96% TD | 97% TD | 97% TD | 97.8% TD | 98.5% TD | 98% TD |
| Color | yellowish | ivory | ivory | ivory | ivory | yellowish | yellow |
| a* | −2.41 | | | | −1.36 | −3.01 | |
| b* | 12.97 | | | | 9.23 | 13.91 | |
| L* | 97.09 | | | | 94.81 | 93.22 | |
| CR % | 99.7 | | | | 99.93 | 99.7 | |
| $K_{IC}$ (MPa m$^{0.5}$) | 14.1 | | 20 | 20 | 6.4 | 9 | |
| Hardness (MPa) | 10800 | | 10100 | 9500 | 11700 | 10300 | |
| Biaxial strength (MPa) | | | | 630 ± 80 | 640 ± 90 | 950 ± 35 | |
| CTE (K$^{-1}$) (100-600° C.) | 11.5 10$^{-6}$ | | | 13.3 10$^{-6}$ | 12.50 10$^{-6}$ | 12.96 10$^{-6}$ | |
| LTD (monoclinic volume fraction in %) | | | | | 0.75 | 1.20 | |

The invention claimed is:

1. Process for preparing a ceramic powder composition comprising zirconia containing $CeO_2$ as a stabilizer, and an aluminate, which process comprises:
   (i) providing an aqueous solution containing salts of zirconium, cerium, aluminum and at least one further metal;
   (ii) adding a base to obtain a precipitate;
   (iii) drying and/or calcining the precipitate; and
   (iv) preparing a dental material from the ceramic powder composition.

2. Process according to claim 1 wherein the dental material comprises dental restorations selected from the group consisting of dental frameworks, dental abutments and dental implants.

3. Process according to claim 1, further comprising forming the ceramic powder by rapid prototyping, stereo lithography or inkjet printing.

4. Process for the preparation of a composite ceramic material comprising a first phase based on zirconia containing $CeO_2$ as a stabilizer, and a second phase based on an aluminate, which process comprises:
   (i) providing a ceramic powder composition comprising zirconia containing $CeO_2$ as a stabilizer, and an aluminate;
   (ii) forming a ceramic body into a dental material for the preparation of dental restorations; and
   (iii) sintering the ceramic body.

5. Process according to claim 4, wherein sintering is performed at a temperature of about 1000 to about 1600° C., for a time of about 15 minutes to about 72 hours.

6. Process according to claim 4, wherein sintering is performed at a temperature of about 1100 to about 1550° C., for a time of about 30 minutes to about 24 hours.

7. Process according to claim 4, wherein sintering is performed at a temperature of about 1400 to about 1500° C., for a time of about 2 to 10 h.

8. Process according to claim 4 wherein the dental restorations comprise dental frameworks, dental abutments and dental implants.

9. Process for the preparation of a composite ceramic material comprising a first phase based on zirconia containing $CeO_2$ as a stabilizer, and a second phase based on an aluminate, which process comprises:
   (i) providing a first slurry comprising zirconia containing $CeO_2$ as stabilizer, a second slurry comprising an aluminate and optionally a third slurry comprising an aluminate which is different from the aluminate of the second slurry;
   (ii) mixing the first slurry with the second and optionally third slurry to obtain a mixed slurry;
   (iii) forming a ceramic body; and
   (iv) sintering the ceramic body.

10. Process according to claim 4, wherein sintering is performed at a temperature of about 1000 to about 1600° C., for a time of about 15 minutes to about 72 hours.

11. Process according to claim 9, wherein sintering is performed at a temperature of about 1100 to about 1550° C., for a time of about 30 minutes to about 24 hours.

12. Process according to claim 9, wherein sintering is performed at a temperature of about 1400 to about 1500° C., for a time of about 2 to 10 h.

13. Process according to claim 9 wherein forming a ceramic body comprises rapid prototyping, stereo lithography or inkjet printing.

* * * * *